United States Patent [19]
Nishioka et al.

[11] Patent Number: 6,086,877
[45] Date of Patent: *Jul. 11, 2000

[54] THERAPEUTIC AGENT FOR RHEUMATIC DISEASE

[75] Inventors: Kusuki Nishioka, Tokyo; Shin Yonehara, Kyoto, both of Japan

[73] Assignee: Santen Pharmaceutical Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/810,593

[22] Filed: Mar. 4, 1997

Related U.S. Application Data

[63] Continuation of application No. 08/533,948, Sep. 26, 1995, abandoned.

[30] Foreign Application Priority Data

Sep. 27, 1994 [JP] Japan ................................. 6-270134

[51] Int. Cl.[7] .................................................. A61K 39/395
[52] U.S. Cl. ..................... 424/156.1; 424/144.1; 424/143.1; 424/142.1; 424/141.1; 424/155.1
[58] Field of Search .............................. 424/130.1, 138.1, 424/144.1, 142.1, 141.1, 172.1, 143.1, 156.1, 155.1; 530/388.1, 388.2, 388.85

[56] References Cited

U.S. PATENT DOCUMENTS

| | | | |
|---|---|---|---|
| 5,464,833 | 11/1995 | Nakai et al. | 514/251 |
| 5,830,469 | 11/1998 | Lynch et al. | 424/144.1 |

FOREIGN PATENT DOCUMENTS

| | | |
|---|---|---|
| 0 510 691 A1 | 10/1992 | European Pat. Off. |
| 58-201712 | 11/1983 | Japan . |
| 60-51105 | 3/1985 | Japan . |
| 2-237935 | 9/1990 | Japan . |
| WO 91/10448 | 7/1991 | WIPO . |
| WO 93/00917 | 1/1993 | WIPO . |
| WO 95/10540 | 4/1995 | WIPO . |

OTHER PUBLICATIONS

Finestein et al, J. Clin. Invest., vol. 96, pp. 1631–1638, (Sep. 1995).
Alderson et al, J. Exp. Med., vol. 178, pp. 2231–2235, (Dec. 1993).
Trauth et al, Science, vol. 245, pp. 301–305, (Jul. 21, 1989).
Yonehara et al, J. Exp. Med., vol. 169, pp. 1747–1756, (May 1989).
Morimoto et al, Cancer Research, vol. 53, pp. 2591–2596, (Jun. 1, 1993).
The Merck Manual of Diagnosis and Therapy, 11th ed., pp. 948–955, (1966).
Lynch et al, CA 123, 81587(e), vol. 123, (1995). [WO 95, 10, 540].
Waldman et al, Science, vol. 252, pp. 1657–1662, (1991).
Chang et al, Science vol. 263, (Mar. 25, 1994), pp. 1759–1762.
Itoh et al, Cell, vol. 66, (Jul. 26, 1991), pp. 233–243.
Nakajima et al., "Induction of Apoptosis and Functional Fas Antigen in Synoviocytes from Patients with Rheumatoid Arthritis", Abstract No. 894, p. S310, *Arthritis & Rheumatism*, vol. 37, No. 9 (Supplement), Sep. 1994.
Heilig et al., "Anti CD95 Mab Induces Apoptosis in Synovial CD45RO+ Cell of Rheumatoid Arthritis Patients", Abstract No. 901, p. S311, *Arthritis & Rheumatism*, vol. 37, No. 9, Abstract No. 901, Sep. 1994.
Itoh et al., "The Polypeptide Encoded by the cDNA for Human Cell Surface Antigen Fas Can mediate Apoptosis", pp. 233–243, *Cell*, vol. 66, 1991.
J.F.R. Kerr, A.H. Wyllie and A.R. Currie, Apoptosis: A Basic Biological Phenomenon With Wide–ranging Implication in Tissue Kinetics, (1972), 239–257, *Br. J. Cancer*, 26.
Tsuneo Saga et al., "In Vitro and In Vivo Properties of Human/Mouse Chimeric Monoclonal Antibody Specific for Common Acute Lymphocytic Leukemia Antigen", (Jun. 1990), 1077–1083, *The Journal of Nuclear Medicine*, 31.
Greg Winter and Cesar Milstein, "Man–made Antibodies", (Jan. 24, 1991), 293–298, *Nature*, 349.
John Savill, Valerie Fadok, Peter Henson and Chris Haslett, "Phagocyte Recognition of Cells Undergoing Apoptosis", (1993), *Immunology Today*, 14.
*Proceedings of the Japanese Cancer Association*, 3rd Annual Meeting, (Oct., 1994), Nagoya, p. 336, No. 1135 (including an English language translation thereof).

*Primary Examiner*—Keith D. MacMillan
*Assistant Examiner*—T. D. Wessendorf
*Attorney, Agent, or Firm*—Frishauf, Holtz, Goodman, Langer & Chick, P.C.

[57] ABSTRACT

The present invention relates to a therapeutic agent for rheumatic disease comprising an anti-Fas monoclonal antibody, or the combination of an anti-Fas monoclonal antibody and a medical substance having an inhibitory effect of cell proliferation as an active ingredient. The anti-Fas monoclonal antibody of this invention reacts with the Fas antigen in synovial cells of patients with rheumatoid arthritis, especially the human Fas antigen specifically and expresses apoptosis on synovial cells.

7 Claims, 3 Drawing Sheets

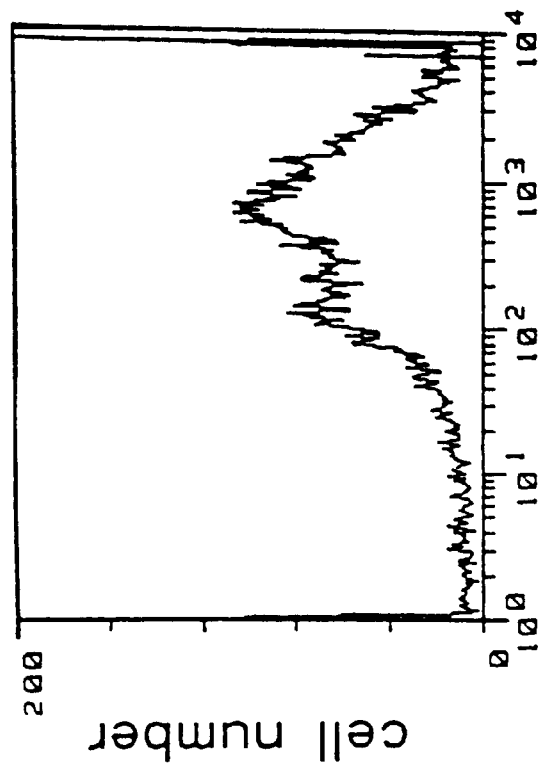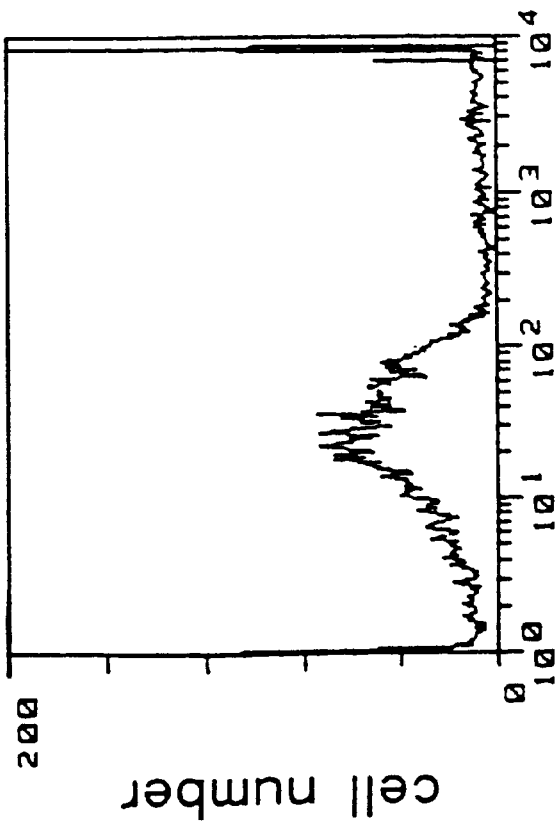

THERAPEUTIC AGENT FOR RHEUMATIC DISEASE

This application is a Continuation of application Ser. No. 08/533,948, Sep. 26, 1995, abandoned.

BACKGROUND OF THE INVENTION

The present invention relates to a therapeutic agent for rheumatic disease comprising an anti-Fas monoclonal antibody, or the combination of an anti-Fas monoclonal antibody and a medical substance having an inhibitory effect on cell proliferation as an active ingredient.

Among various rheumatic disorders, especially rheumatoid arthritis (RA) belongs to the group of diseases in which the basic pathogenesis is abnormal proliferation of synovial cells accompanied by various immunological disorders caused by internal and external factors and developed to bone and joint erosion.

RA is also characterized by regression of the hyperplastic synovium with subsequent replacement by fibrotic tissue (Fassbender HG: "Pathology of Rheumatic Diseases", Berlin, Heidelberg, Springer-Verlag, 1975), but the mechanisms of regression and replacement remain obscure. However, the destruction of tissue around morbid joints in RA is considered to be caused by abnormal production of cytokines from inflammatory synovial cells.

Synovial cells play an important role in RA in this way. For example, examining the findings of joint lesions with RA, an increase in synovial villi and multi-layerization of synovial cells have been observed and synovial cells are proliferated (Daniel J. McCarty, "Arthritis and Allied Conditions, A Textbook of Rheumatology", 11th Ed.).

If the proliferation of these synovial cells can be inhibited by a medical substance, it is thought to be a therapeutic agent for rheumatic disease.

At present, anti-inflammatory agents such as steroid, gold, and several cytotoxic agents are used for treating RA, but a medical substance which inhibits proliferation of synovial cells specifically is not known yet.

On the other hand, programmed cell death named "apoptosis" by Kerr et al., is distinct from necrosis (Br. J. Cancer, 26,239 (1972)). Necrosis of cells passes through a process accompanied by liberation of cytoplasmic contents, etc. because of hyperthermia, response to an antibody with complement, or chemical mediators. On the other hand, programmed cell death is observed in a certain group of cells programmed previously to die out in vivo, and it passes through a process termed apoptosis accompanied by phenomena such as bending of cell surface, condensation of nuclear chromatin, and chromosome DNA ladder formation.

Recently, Yonehara et al. reported an anti-Fas monoclonal antibody against a Fas antigen which is a cell membrane molecule concerned with apoptosis of immunocompetent cells (J. Exp. Med., 169, 1747 (1989)). Krammer et al. reported an anti-APO-1 antibody as an antibody which combines specifically with an antigen accompanied by apoptosis (Science, 245, 301 (1989)), but it was afterward confirmed that the antigens which these antibodies recognize are the same (Cell, 66, 233 (1991)).

Various studies were made about applications of the anti-Fas antibody including a therapeutic agent for AIDS and tumors (Japanese Patent Laid-open Publication No. 2-237935; WO 91/10448).

As described above, pathogenesis of RA is characterized by abnormal proliferation of synovial cells with infiltration of inflammatory cells and bone erosion. However, the proliferation of synovial cells is not limitless and spontaneous suppression of synovial proliferation is observed. Accordingly, it is necessary to study how alteration of rheumatoid synovial tissue occurs, whether the alteration is mediated by programmed cell death (apoptosis), and whether the Fas antigen exists in synovial cells. These studies are necessary to support this invention theoretically.

The subject of this invention is to develop a use for the anti-Fas monoclonal antibody as a therapeutic agent for rheumatic disease, especially as a therapeutic agent for rheumatoid arthritis, therefore, the following subject matters have to be studied.

1) Whether the anti-Fas monoclonal antibody can induce apoptosis in RA synovial cells,
2) Whether the anti-Fas monoclonal antibody is effective for treatment of RA,
3) Whether the anti-Fas monoclonal antibody does not cause severe side effects on other cells and organs.

If apoptosis is observed in RA synovial cells, if the abnormal proliferation of synovial cells can be inhibited by inducing apoptosis in synovial cells specifically, if the effectiveness of the medicine for human RA can be predicted, and if the medicine does not show severe side effects on other cells and organs, the medicine is expected to be a radical therapeutic agent for RA.

However, a medicine which induces apoptosis in synovial cells is not known yet, and it has been an important subject matter to find a medicine which inhibits the abnormal proliferation of synovial cells specifically.

SUMMARY OF THE INVENTION

In accordance with a first aspect of the present invention a new therapeutic agent for rheumatic disease is provided, which comprises an anti-Fas monoclonal antibody, an active ingredient, which reacts with a Fas antigen in rheumatoid synovial cells specifically and induces apoptosis, which means a morphology of programmed cell death, in synovial cells.

The preferred anti-Fas monoclonal antibody is a monoclonal antibody which reacts with a human Fas antigen specifically.

Preferably the above-mentioned anti-Fas monoclonal antibody is an antibody which is produced by a hybridoma cell clone obtained by immunizing with human diploid fibroblast, especially an antibody which is produced by a cell clone CH-11 obtained by immunizing mice with human diploid fibroblast, and then fusing mouse splenic cells with mouse myeloma cells.

According to the other aspect of the present invention, a new therapeutic agent for rheumatic disease is provided, which comprises the combination of an anti-Fas monoclonal antibody and a medical substance having an inhibitory effect on cell proliferation.

The preferred medical substance having the inhibitory effect on cell proliferation is actinomycin D.

The agent according to the present invention is preferably in the form of intraarticular injection.

To solve the above-mentioned subject matters, the inventors first observed alteration of synovial tissue of patients with RA and found that apoptosis appears in synovial cells and that the Fas antigen occurs in synovial cells. Then the inventors examined whether apoptosis is induced in the abnormal proliferating synovial cells of patients with RA by adding the anti-Fas monoclonal antibody. As a result, the proportion of apoptosis in the proliferating synovial cells of patients with RA was much larger than that in synovial cells of non-RA patients. This result indicates that the anti-Fas monoclonal antibody does not act on normal synovial cells very much and that it leads the proliferating synovial cells to apoptosis specifically.

The present invention especially relates to the anti-Fas monoclonal antibody which reacts with the human Fas antigen specifically, and it is necessary to administer it to human to examine its clinical effect, but it is impossible to administer it to human easily. The inventors succeeded in prediction of the effectiveness of the anti-Fas antibody for humans by administrating a mouse anti-Fas antibody immunized with a mouse Fas antigen to mice and examining its effect.

In addition, examining whether the anti-Fas monoclonal antibody used in this invention does not cause severe side effects on other cells and organs, this antibody was found to have little problem of such side effects.

It was also proved that the proportion of apoptosis in synovial cells of patients with RA increases when actinomycin D, which is a medicine having an inhibitory effect of cell proliferation, is added to the anti-Fas monoclonal antibody.

BRIEF DESCRIPTION OF THE DRAWINGS

FIGS. 4(A) and 4(B) are graphs of flow cytometry analysis with FIG. 4(A) being the control and FIG. 4(B) showing the expression of Fas antigen on cultured synovial cells of patients with RA.

DESCRIPTION OF THE PREFERRED EMBODIMENT

Figure 1:
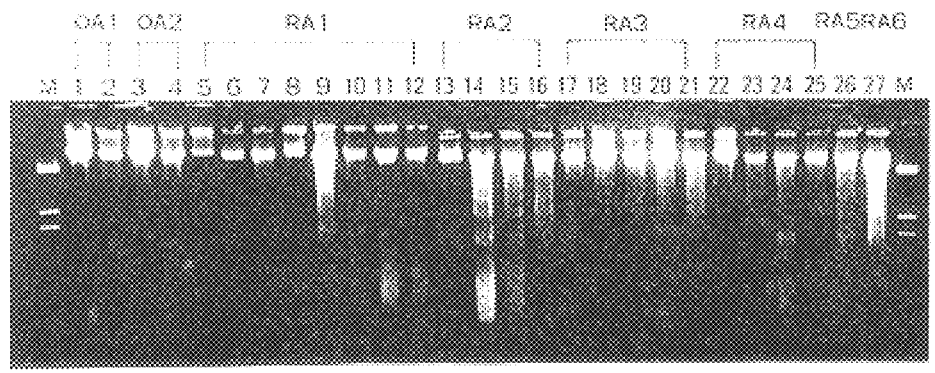
FIG. 1 is a photograph of electrophoresis showing typical DNA ladder formation in which DNA extracted from fresh synovial cells of patients with rheumatoid arthritis (RA) indicates apoptosis and showing that DNA from patients with osteoarthritis does not show ladder formation.

The present invention relates to a therapeutic agent for rheumatic disease comprising the anti-Fas monoclonal antibody, or the combination of the anti-Fas monoclonal antibody and a medical substance having an inhibitory effect of cell proliferation as an active ingredient.

Explaining greater in detail, the anti-Fas monoclonal antibody of this invention reacts with the Fas antigen in synovial cells of patients with RA, especially the human Fas antigen specifically and induces apoptosis of synovial cells.

The anti-Fas monoclonal antibody used for this invention was produced from, for example, a hybridoma cell clone obtained by immunizing with human diploid fibroblast. This anti-Fas monoclonal antibody can be prepared according to, for example, the method of Yonehara et al.(J. Exp. Med., 169, 1747 (1989)). The anti-Fas monoclonal antibody produced from hybridoma "clone CH-11" obtained by fusing BALB/c mouse splenic cells immunized with human diploid fibroblast FS-7 with mouse myeloma cells (NS-1) was used for practical tests. This anti-Fas monoclonal antibody is commercially available from Medical & Biological Laboratory Co. The property of this available antibody is IgM fractionation from ascites. The ascites were obtained by inoculating "clone CH-11" on BALB/c mice and the IgM fraction was purified by affinity chromatography.

The anti-Fas monoclonal antibody prepared by a similar method to that of Yonehara et al. using the human Fas antigen instead of FS-7 used for the method of Yonehara et al.(J. Exp. Med., 178, 2231 (1993)) can be also used.

Anti-Fas monoclonal antibody used for various tests of this invention is described above, but this antibody can be also used in the form of a chimera antibody, in which V (variable) regions derived from mouse are left intact and C (constant) regions are replaced with C regions derived from human, and it can be also used in the form of a CDR (complementarity-determining region)-grafted antibody, in which CDR regions derived from mouse are left intact and the other whole regions are replaced with regions derived from human.

The conversion of antibody derived from mouse into the chimera antibody or the CDR-grafted antibody can be performed according to known methods (J. Nucl. Med., 31, 1077 (1990); Nature, 349, 293 (1991); etc.).

The object of this invention is medical treatment for rheumatic disease by use of the anti-Fas monoclonal antibody which reacts with the human Fas antigen specifically and induces apoptosis of synovial cells. This invention includes any converted antibodies, so long as active regions of the antibody are kept.

If a substance can induce apoptosis in synovial cells of rheumatoid joints and can inhibit the proliferation of synovial cells, this substance is expected to be an excellent therapeutic agent for RA.

Accordingly, to detect the appearance of apoptosis on rheumatoid synovial cells, the inventors first examined DNA ladder formation in synovial tissue samples obtained from patients with RA and patients with osteoarthritis (OA) as a contrast.

As a result, DNA ladder formation that is characteristic of apoptosis was observed only in patients with RA, not in patients with OA. The cells showing the DNA ladder formation in synovium from patients with RA were the adherent synovial cells of synovia, not the infiltrating cells. These findings were supported by electron microscopic analysis and the nick end labeling method which recognizes the characteristic of apoptotic cell death.

Observing alteration of synovial tissue of patients with RA with electron microscope, typical apoptotic synovial cells were detected in synovial tissue of patients with RA. These apoptotic cells were adjacent to synovial type A cells. This phenomenon is compatible with pathology of apoptosis, in which apoptotic cells are recognized by adjacent macrophages, etc.(Savill, Immunol. Today 14, 131 (1993)).

Additionally, by nick end labeling method, the biotinylated dUTP-labelled cells were confirmed to be synovial fibroblasts, not infiltrating mononuclear cells in RA synovium. These positive cells were mainly detected in synovial tissue intima, and these results indicate that RA synovial cells exhibit apoptosis in situ. On the other hand, positive cells were not detected in patients with OA.

Performing flow cytometric analysis using cultured rheumatoid synovial cells to examine whether the Fas antigen is detected in synovial cells, the Fas antigen was detected.

These results suggest that apoptosis occurs in synovial cells of patients with RA and that the Fas antigen participates in apoptosis.

An experiment was then performed to examine whether apoptosis occurs in synovial cells by adding the anti-Fas monoclonal antibody to synovial cells from joints of patients with RA. Though detailed data are shown in the article of tests mentioned later, apoptosis hardly occured in human synovial cells other than patients with RA, whereas the proportion of apoptosis increased with the concentration of the added anti-Fas monoclonal antibody in synovial cells of patients with RA. This result indicates that the anti-Fas monoclonal antibody does not act on normal cells essentially and that it can lead the proliferating synovial cells to apoptosis specifically.

The effect of the anti-Fas monoclonal antibody is expected to increase in combination with medicines having inhibitory effects of cell proliferation. Actinomycin D, mitomycin C, cycloheximide, interferon gamma, etc. are given as medical substances having inhibitory effects of cell proliferation. As a typical example, actinomycin D was added to the anti-Fas antibody. Adding the obtained mixture to synovial cells of patients with RA, the proportion of apoptosis was found to increase remarkably.

To predict the clinical effect of the anti-Fas monoclonal antibody of this invention on human, an anti-mouse Fas monoclonal antibody (Medical & Biological Laboratory Co.) was administered to mouse disease models. The antibody was produced from "clone RK-8" obtained by fusing splenic cells of hamsters immunized with a mouse Fas antigen with mouse myeloma cells. As a result, a clear curing effect was obtained. This finding can predict sufficiently the clinical effect of the anti-Fas monoclonal antibody of this invention on human.

This anti-mouse Fas monoclonal antibody was injected (5 µg/mouse) into mouse cavum articulare of paw and expression of toxicity was examined. However a disorder was not observed in the thymus, kidney, lung, spleen, and heart. The anti-Fas monoclonal antibody used in this invention was found not to cause severe side effects on other cells and organs practically.

The indispensable requirement of the anti-Fas monoclonal antibody of this invention is to have a property of reacting with the Fas antigen in synovial cells of patients with RA specifically and inducing apoptosis in synovial cells. The inventors found that there are both antibodies satisfying and not satisfying the above-mentioned indispensable requirement of this invention among anti-Fas monoclonal antibodies. For example, after mice were immunized with a recombinant Fas antigen obtained from mouse cells transformed with a human Fas antigen cDNA, the anti-Fas monoclonal antibody was obtained from hybridoma "clone ZB4" obtained by fusing mouse splenic cells with mouse myeloma cells. Examining whether this antibody induces apoptosis in synovial cells of patients with RA, this antibody was found not to induce apoptosis practically. In addition, this antibody was not found to induce apoptosis but found to counteract the effect of the anti-Fas monoclonal antibody which induces apoptosis.

This result supports that the above-mentioned definition is correct and suitable as a definition of the anti-Fas monoclonal antibody of this invention. An antibody (Medical & Biological Laboratory Co.) prepared from "clone CH-11", an antibody (Bender+Co Ges mbH) named anti-APO-1/Fas (inducing), etc. are given as examples of antibodies which induce apoptosis. But the anti-Fas monoclonal antibody of this invention only has to have the property described above, and is not limited to these examples.

The anti-Fas monoclonal antibody is usually administered by injection into the knee joint, shoulder joint, etc. in the form of an intraarticular injection, but it can be administered orally or rectally. The dosage of the anti-Fas monoclonal antibody is adjusted depending on symptom, dosage form, etc. It can be 0.1 to 10 ml in concentration of 0.0001 to 1.0% by weight in the case of injection, and the usual daily dosage can be 0.001 to 10 mg in one or few divided doses in the case of oral agent. The dosage of the medicine having an inhibitory effect of cell proliferation to be added to the anti-Fas monoclonal antibody can be 0.00001 to 0.1% by weight in the case of injection, and usual daily dosage can be 0.0001 to 1 mg in the case of an oral agent.

Formulations of the anti-Fas monoclonal antibody can be prepared in the usual way. In the case of injection, excipients used usually such as osmotic pressure adjustor, e.g., sodium chloride, pH adjustor, e.g., sodium phosphate, surfactant, e.g., Polysorbate 80, and thickening agent, e.g., methyl cellulose can be added optionally to the anti-Fas monoclonal antibody and dissolved in distilled water for injection. A formulation can be also prepared in the form of dissolution just before using. In the case of a tablet, excipients used usually such as an extending agent, e.g., lactose, binder, e.g., crystalline cellulose, polyvinyl pyrrolidone, or a lubricant, e.g., magnesium stearate can be added to the anti-Fas monoclonal antibody. Liposome preparations which can transfer medicines to diseased lesions effectively, namely formulations included in fatty emulsion can be also used as disclosed in Japanese Patent Laid-open Publication No. 60-51105, 58-201712, etc. Examples of formulations are shown as follows.

EXAMPLES

Some examples of formulation containing anti-Fas monoclonal antibody of this invention are shown as follows, 1) Injection

| Formulation 1 (in 100 ml) | |
|---|---|
| anti-Fas monoclonal antibody | 0.01 g |
| sodium chloride | 0.9 g |
| distilled water for injection | q.s. |
| Formulation 2 (in 100 ml) | |
| anti-Fas monoclonal antibody | 0.001 g |
| sodium chloride | 0.9 g |
| methyl cellulose | 0.5 g |
| distilled water for injection | q.s. |
| Formulation 3 (in 100 ml) | |
| anti-Fas monoclonal antibody | 0.01 g |
| actinomycin D | 0.005 g |
| sodium chloride | 0.9 g |
| distilled water for injection | q.s. |

2) Tablet

| Formulation 1 | |
|---|---|
| anti-Fas monoclonal antibody | 1 mg |
| lactose | 133 mg |
| crystalline cellulose | 30 mg |
| polyvinyl pyrrolidone K30 | 5 mg |
| magnesium stearate | 1 mg |
| total | 70 mg |
| Formulation 2 | |
| anti-Fas monoclonal antibody | 0.1 mg |

-continued

| | |
|---|---|
| actinomycin D | 0.02 mg |
| lactose | 133.88 mg |
| crystalline cellulose | 30 mg |
| polyvinyl pyrrolidone K30 | 5 mg |
| magnesium stearate | 1 mg |
| total | 170 mg |

The results of various tests are shown as follows to demonstrate the effect of this invention.

Tests

1. Detection of Appearance of Apoptosis in Rheumatoid Synovial Cells

Method of Experiment

Synovial tissues were obtained from patients diagnosed as having RA according to the criteria of the American College of Rheumatology and synovial cells were collected according to the method of Goto et al. (J. Clin. Invest., 80, 786 (1987)). Namely, the synovial tissue was minced into small pieces and digested with collagenase (Sigma Chemical Co., St. Louis, Mo.). The single cell suspension was incubated overnight, and then the floating cells were separated as the non-adherent infiltrating cells of the synovium. On the other hand, adherent cells, namely, synovial cells were cultured in dishes until examination. Synovial cells of patients with osteoarthritis (OA) were used as a contrast.

Secondly, DNA extraction from cells and electrophoresis to detect DNA ladder formation were performed according to the literature (Science, 257, 217 (1992); Nucleic Acids Res., 3, 2303 (1976)) to confirm whether apoptosis occurs in these cells. Namely, cells were incubated in 0.5 mg/ml protinase K (Sigma Chemical Co.)-TNE (10 mM Tris pH 7.5, 0.1 M sodium chloride, 1 mM EDTA)-SDS solution at 50° C. for one hour, then treated with 0.1 mg/ml RNase A (Nippongene, Tokyo, Japan) for additional one hour. Then, 10 $\mu$l of DNA was electrophoresed on a 1.5% agarose gel, stained with ethidium bromide and observed.

Results

All samples of DNA extracted from synovial cells of patients with RA exhibited DNA ladder formation typical of apoptosis.

Synovial tissue of patients with RA was then treated with collagenase to give the following two types of cells, non-adherent infiltrating cells and adherent cells (synovial cells). Observing these two types of cells, DNA ladder formation was recognized only in adherent cells. The result of agarose gel electrophoresis of DNA described above is shown in FIG. 1.

On the other hand, DNA ladder formation was not observed in synovial cells of patients with OA.

In FIG. 1, OA1 and OA2 indicate DNA from patients with OA, and RA1–RA6 indicate DNA from patients with RA, respectively. In numbered lanes, lanes 2 and 4 indicate DNA from synovial cells of knee joints of patients with OA, lanes 9, 11, 21 and 26 indicate DNA from synovial cells of knee joints of patients with RA, lanes 10, 14, 25 and 27 indicate DNA from synovial cells of elbow joints, lanes 12 and 15 indicate DNA from synovial cells of wrist joints, lanes 16, 20, 23 and 24 indicate DNA from synovial cells of finger joints, and lanes 18 and 19 indicate DNA from synovial cells of ankle joints. Since the other lanes do not relate to this article directly, the assignment of them is omitted. The ladder formation was observed in DNA from joints of patients with RA described above, whereas the ladder formation was not observed in DNA from joints of patients with OA. 2. Detection of Apoptosis by Electron Microscopic Analysis and DNA Nick end Labeling Method Method of Experiment Synovial tissues obtained from patients with RA and patients with OA were fixed with 2.5% glutaraldehyde and assessed for electron microscopic analysis. DNA nick end labeling of tissue sections was performed according to the method of Gavrieli et al. (J. Cell Biology, 119, 493 (1992)).

Namely, synovial tissues were fixed in 4% buffered formaldehyde and embedded in paraffin. Paraffin sections (4-6 $\mu$m) were applied to slides pretreated with a 0.01% aqueous solution of polylysine (300,000 mol. by weight, Sigma Chemical Co.). The slides were then deparaffinized and the tissues were hydrated. Proteins were stripped from the nuclei by incubating the tissue with 20 $\mu$g/ml proteinase K at room temperature. Endogenous peroxidase was quenched with 2% hydrogen peroxide. These samples were immersed in terminal deoxynucleotidyl transferase (TDT) buffer (30 mM Trizma base, pH 7.2, 140 mM sodium cacodylate, 1 mM cobalt chloride). Then, TDT (0.3 u/ $\mu$l ) and biotinylated-dUTP in TDT buffer were added. The reaction was terminated by placing the slides in TB buffer (300 mM sodium chloride, 30 mM sodium citrate) and samples were covered with a 2% aqueous solution of human serum albumin (HSA) or bovine serum albumin (BSA), followed by Extra-avidin Peroxidase. Finally, the samples were stained with AEC.

Results

Figure 2:
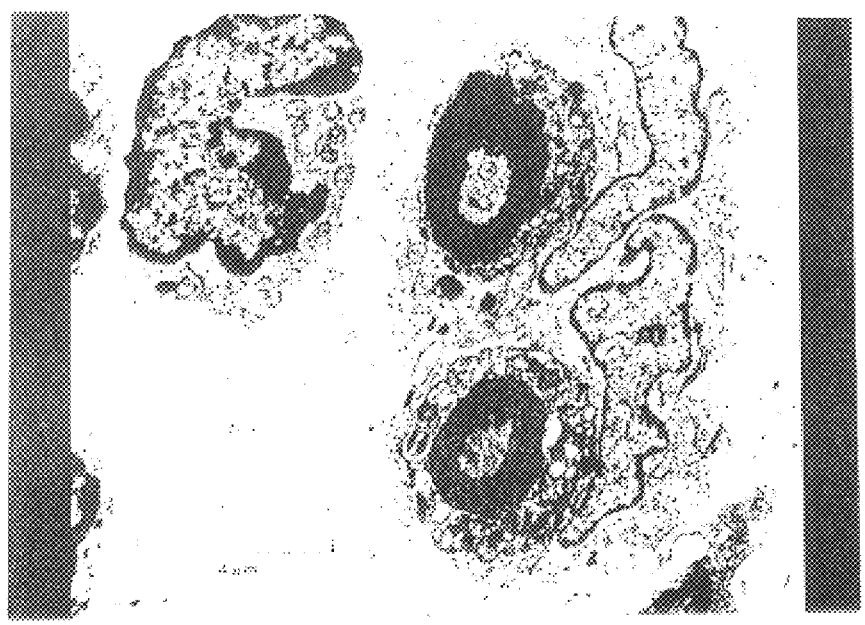
FIG. 2 is a photograph of electron microscope showing a typical morphology of apoptosis in synovial tissue of patients with RA.

The photograph of detection with an electron microscope is shown in FIG. 2.

As apparent from FIG. 2, the typical morphology of apoptosis, i.e., tightly packed cytoplasmic organelles and dense chromatin bound along the nuclear envelope, was observed in synovial tissues of patients with RA by electron microscopy. In addition, synovial type A cells (tissue macrophage like cells) were found adjacent to these apoptotic cells.

On the other hand, no change by typical apoptosis was observed in synovial tissues of patients with OA.

Figure 3A:
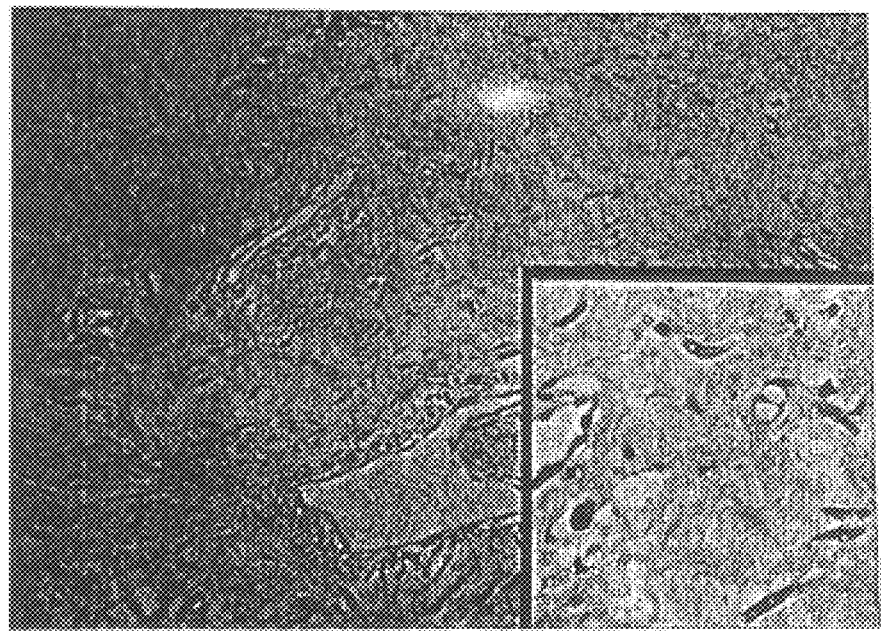
FIG. 3A is a photograph of synovial tissue of patients with RA stained with hematoxylin-eosin.
Figure 3B:
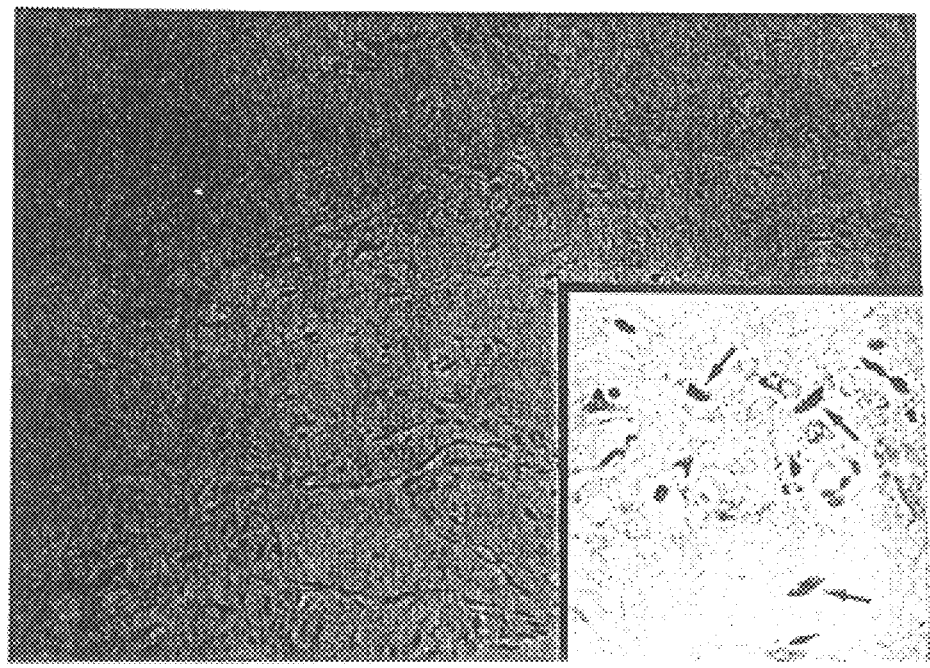
FIG. 3B is a photograph of synovial tissue of the same patients treated by nick end labeling method.

The photograph of synovial tissue of patients with RA stained with hematoxylin-eosin is shown in FIG. 3A, and the photograph of synovial tissue of the same patients treated with nick end labeling method and stained is shown in FIG. 3B.

As shown with an arrow in FIG. 3B, nuclei of fibroblastoid cells were stained in the synovial tissues, whereas non-infiltrating mononuclear cells were not stained.

3. Flow Cytometric Analysis of Fas Antigen

Method of Experiment

Cell surface Fas antigen was detected as follows. Synovial cells ($5 \times 10^5$) from patients with RA and patients with OA were washed with isotonic phosphate buffered saline (PBS), then suspended in 0.1 ml PBS containing 1% bovine serum albumin, 0.02% sodium azide, and 20 $\mu$l/ml anti-Fas monoclonal antibody (Medical & Biological Laboratory Co., Nagoya, Japan, produced from "clone CH-11"), and placed on ice for 30 min. After washing twice with PBS, cells were incubated for 30 min with 0.1 ml PBS containing 1% bovine serum albumin, 0.02% sodium azide, and 10 $\mu$g/ml affinity-purified FITC-labeled goat anti-mouse IgM. Cells were then washed three times with PBS and analyzed with a flow cytometer.

A similar experiment was performed with a sample to which mouse IgM was added instead of the anti-Fas monoclonal antibody as a control for a comparison.

Results

The obtained results are shown in FIGS. 4(A) and 4(B). It is apparent from FIG. 4(B) that the sample to which the anti-Fas monoclonal antibody was added had stronger color development than the control sample results depicted in FIG. 4(A), and the Fas antigen was proved to express on synovial cells of patients with RA. A similar result was obtained in the case of patients with OA.

4. Induction of Apoptosis in Synovial Cells by Adding of Anti-Fas Monoclonal Antibody Method of Experiment D-MEM (Dulbecco's Modified Eagle Medium) solution, and then the anti-Fas monoclonal antibody (Medical & Biological Laboratory Co., produced from "clone CH-11", PBS containing 50% glycerol) were added to synovial cells ($1\times10^6$) of patients with RA obtained by the above-mentioned test 1 until the concentration finally reached 0.01–1.0 µg/ml, and these cells were incubated at 37° C. for 24 hours. These cells were then stained with trypan blue, viable cells were quantified by phase-contrast microscopy, and the proportion of apoptosis was determined on the basis of the number of dead cells. Similar experiments were performed using synovial cells of patients with OA and normal human (patients with meniscitis) as contrasts.

DNA extraction from cells and electrophoresis to detect DNA ladder formation were then performed by the same method as that used for the above-mentioned test 2 to confirm whether apoptosis occurs in the dead cells from the sample to which the anti-Fas monoclonal antibody was added.

A constant quantity of actinomycin D (50 ng/ml) was added to the anti-Fas monoclonal antibody, this sample was added to the synovial cells of patients with RA, and an experiment was performed in a same manner as above.

Results

The proportion of apoptosis in the synovial cells with addition of only anti-Fas monoclonal antibody is shown in Table 1.

TABLE 1

| | Addition of anti-Fas monoclonal antibody (µg/ml) | Proportion of apoptosis | | |
|---|---|---|---|---|
| | | Patients with RA | Patients with OA | Normal |
| Anti-Fas monoclonal antibody | 0.01 | 5.5% | 1.7% | 1.1% |
| | 0.1 | 25.8% | 2.2% | 0.9% |
| | 1.0 | 45.2% | 3.2% | 2.9% |

As shown in Table 1, it was found that the synovial cells except for those of patients with RA are hardly subject to the action of the anti-Fas monoclonal antibody, whereas cell death increases with the concentration of the anti-Fas monoclonal antibody in the synovial cells of patients with RA. It was also confirmed that the cell death is caused by apoptosis because DNA ladder formation was detected by the experiment using electrophoresis.

The results with addition of actinomycin D to the anti-Fas monoclonal antibody are shown in Table 2.

TABLE 2

| | Addition of anti-Fas monoclonal antibody (µg/ml) | Proportion of apoptosis Patients with RA |
|---|---|---|
| Anti-Fas monoclonal | 0.01 | 60.4% |
| | 0.1 | 83.0% |

TABLE 2-continued

| | Addition of anti-Fas monoclonal antibody (µg/ml) | Proportion of apoptosis Patients with RA |
|---|---|---|
| antibody + Actinomycin D | 1.0 | 93.7% |

As apparent from Table 2, the proportion of cell death was remarkably increased in the case of combined use of the anti-Fas monoclonal antibody and actinomycin D compared to that in the case of the anti-Fas monoclonal antibody alone.

These results exhibit that the anti-Fas monoclonal antibody induces apoptosis in the proliferating synovial cells, and the anti-Fas antibody was proved to be an excellent therapeutic agent for RA because the anti-Fas antibody hardly or very weakly acts on cells except for those of patients with RA.

5. In Vivo Test Using Mouse Models

To predict the clinical effect of the anti-Fas monoclonal antibody on human, the anti-Fas monoclonal antibody was administered to mouse disease models and the effect was examined.

Antibody

The anti-mouse Fas monoclonal antibody which was used (Medical & Biological Laboratory Co.) was prepared as follows. Armenian hamsters were immunized with a recombinant soluble mouse Fas antigen and the splenic cells from immunized hamsters were fused with the mouse myeloma cells (NS-1) to give hybridoma "clone RK-8". The anti-mouse Fas monoclonal antibody is a monoclonal IgG antibody which was obtained from the hybridoma and was purified.

Disease Models

BALB/CAnN Px transgenic mouse (10–20 weeks old, strain was maintained in Nippon Institute for Biological Science) arthritis models approximated to human RA were used.

Method of Experiment

5 µl of anti-mouse Fas monoclonal antibody (1 mg/ml, phosphate buffered saline) was injected into the mouse cavum articulare of paw the and the quantity of paw swelling was measured. The width of joint and the height of instep were measured with slide calipers and the product of the width and the height was defined as the quantity of paw swelling. Purified hamster IgG (UCX8-4B3, Pharmingen) was used as a control.

Results

Results are shown in Table 3. The values in Table 3 averages of percentages of paw swelling to the control before administration.

TABLE 3

| Days after administration | Antibody administered group (n = 5) | Control group (n = 4) |
|---|---|---|
| 0 | 100 | 100 |
| 1 | 87 | 98 |
| 2 | 79 | 101 |
| 3 | 75 | 100 |
| 4 | 74 | 98 |

As shown in Table 3, the antibody administered group decreased paw swelling significantly.

6. Test of Induction of Apoptosis

To investigate specificity of induction of apoptosis by the anti-Fas monoclonal antibody, the effect of two kinds of anti-Fas monoclonal antibodies on synovial cells of patients with RA was examined.

Antibody

The anti-Fas monoclonal antibody (the same antibody as that used for the above-mentioned test 4, referred to as "antibody A" hereinafter) produced from "clone CH-11", and one more anti-Fas monoclonal antibody (Medical & Biological Laboratory Co., referred to as "antibody B" hereinafter) were used. The latter was produced from "clone ZB4" obtained by the method including the following two steps; immunizing BALB/c mice with a recombinant Fas antigen obtained from mouse cells transformed with a human Fas antigen cDNA, and then fusing the mouse splenic cells with mouse myeloma cells (NS-1).

Method of Experiment

Synovial cells ($1\times10^5$) of patients with RA obtained by the same method as that used for the above-mentioned test 1 were incubated in cell culture plate. After cell adhesion, antibody A (0.1 µg/ml, 1 µg/ml) or antibody B (0.5 µg/ml) was added thereto and survival rates of cells were determined after a certain period of time. In addition, antibody B (0.5 µg/ml) was added first, and then antibody A (0.1 µg/ml, 1 µg/ml) was added one hour after, and survival rates of cells were determined after a certain period of time (represented in period of time after addition of antibody A).

Results

Results are shown in Table 4.

TABLE 4

| antibody | Survival rate of cells (%) | | |
|---|---|---|---|
| | After 6 hr | After 24 hr | After 48 hr |
| A (0.1 µg/ml) | 85 | 69 | 77 |
| A (1.0 µg/ml) | 71 | 54 | 59 |
| B (0.5 µg/ml) | 98 | 98 | 99 |
| A (0.1 µg/ml) + B (0.5 µg/ml) | 98 | 97 | 98 |
| A (1.0 µg/ml) + B (0.5 µg/ml) | 98 | 98 | 97 |

As shown in Table 4, antibody A induces apoptosis in synovial cells depending on the concentration (it tends to recover after 48 hours), whereas antibody B hardly induces apoptosis. In addition, antibody B indicates antagonism against antibody A and counteracts the effect of antibody A.

What is claimed is:

1. A method of treatment for rheumatoid arthritis comprising administering to a patient in need thereof, (a) an amount of an anti-Fas monoclonal antibody isotype IgM which is effective for treating rheumatoid arthritis and which reacts with a Fas antigen in rheumatoid synovial cells specifically and induces apoptosis, (b) with an excipient.

2. A method of treatment for rheumatoid arthritis comprising administering to a patient in need thereof a combination of an amount of an anti-Fas monoclonal antibody isotype IgM which is effective for treating rheumatoid arthritis and a pharmaceutically effective amount of a compound having an inhibitory effect on cell proliferation, said compound being selected from the group consisting of Actinomycin D, mitomycin C, cycloheximide and interferon gamma.

3. The method of claim 1, wherein said anti-Fas monoclonal antibody isotype IgM is an antibody which is produced from a cell clone obtained by immunizing with a human diploid fibroblast.

4. The method of claim 1, wherein said anti-Fas monoclonal antibody isotype IgM is an antibody which is produced from cell clone CH-11 obtained by immunizing a mouse with a human diploid fibroblast, and then fusing the resultant mouse splenic cells with mouse myeloma cells.

5. The method of claim 1, wherein said administering is in the form of an intraarticular injection.

6. The method of claim 2, wherein the compound having an inhibitory effect on cell proliferation is Actinomycin D.

7. The method of claim 6, wherein 0.02 to 0.005 g of the Actinomycin D are administered per 1 g of the anti-Fas monoclonal antibody isotype IgM.

* * * * *